United States Patent [19]

Manes

[11] 4,149,402
[45] Apr. 17, 1979

[54] ANALYTICAL METHOD FOR DETERMINING DESORPTION ISOTHERM AND PORE SIZE DISTRIBUTION OF AN ABSORBENT MATERIAL

[76] Inventor: Milton Manes, 1613 Chadwick Dr., Kent, Ohio 44240

[21] Appl. No.: 865,337

[22] Filed: Dec. 28, 1977

[51] Int. Cl.$^2$ .......................................... G01N 31/08
[52] U.S. Cl. ............................................... 73/23.1
[58] Field of Search ................ 73/23.1, 23; 23/232 C, 23/254 R

[56] References Cited

U.S. PATENT DOCUMENTS

| | | | |
|---|---|---|---|
| 2,985,007 | 5/1961 | Boeke | 73/23.1 |
| 3,211,006 | 10/1965 | Haley | 73/23.1 |

OTHER PUBLICATIONS

Blumer: "Thermometric Monitor for Chromatographic Streams," *Analytical Chemistry*, vol. 32, No. 7, pp. 772-776, 6/1960.

Burke et al., "Computer Acquisition of Frontal Analysis Chrom. Data for Surface Area Determination," *Anal. Chem.*, vol. 43, No. 4, Apr. 1971, pp. 573-578.

*Primary Examiner*—Stephen A. Kreitman
*Attorney, Agent, or Firm*—Cushman, Darby & Cushman

[57] ABSTRACT

A method is provided for generating data for use in calculating a desorption isotherm for an adsorbent material as well as a pore size distribution characteristic of the adsorbent material by flowing an adsorbate gas over a sample in a cell until the surface of the sample is saturated with the adsorbate, shutting off the flow of the adsorbate gas and then flowing a carrier gas through the cell to remove the adsorbate material from the surface of the sample while continuously detecting and recording per unit of time the composition of the gas mixture flowing from the cell and the sample temperature until only the carrier gas is detected.

5 Claims, 3 Drawing Figures

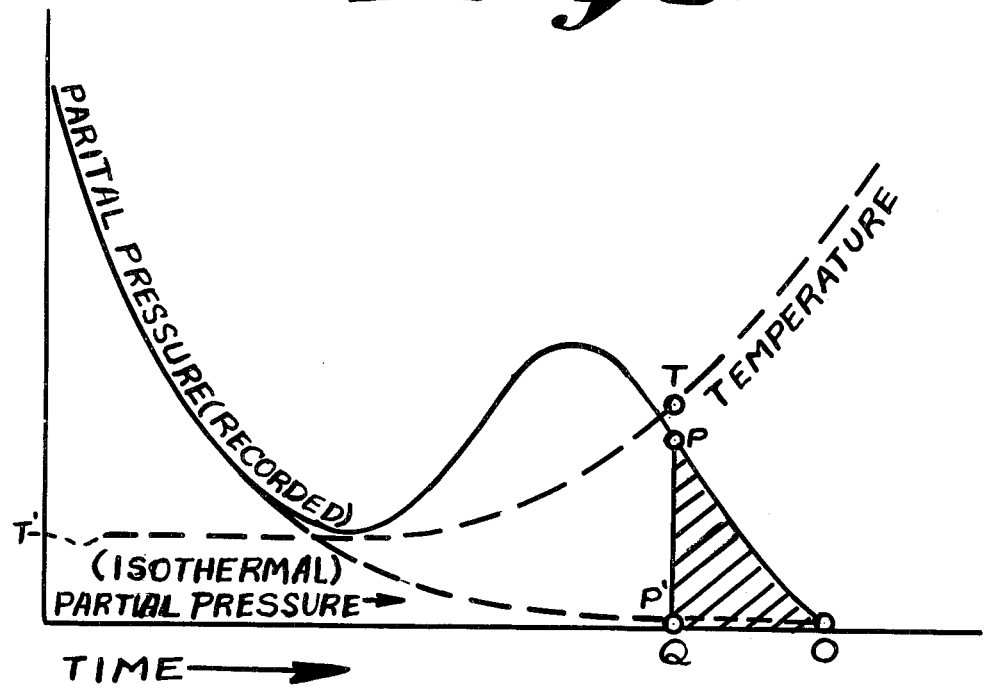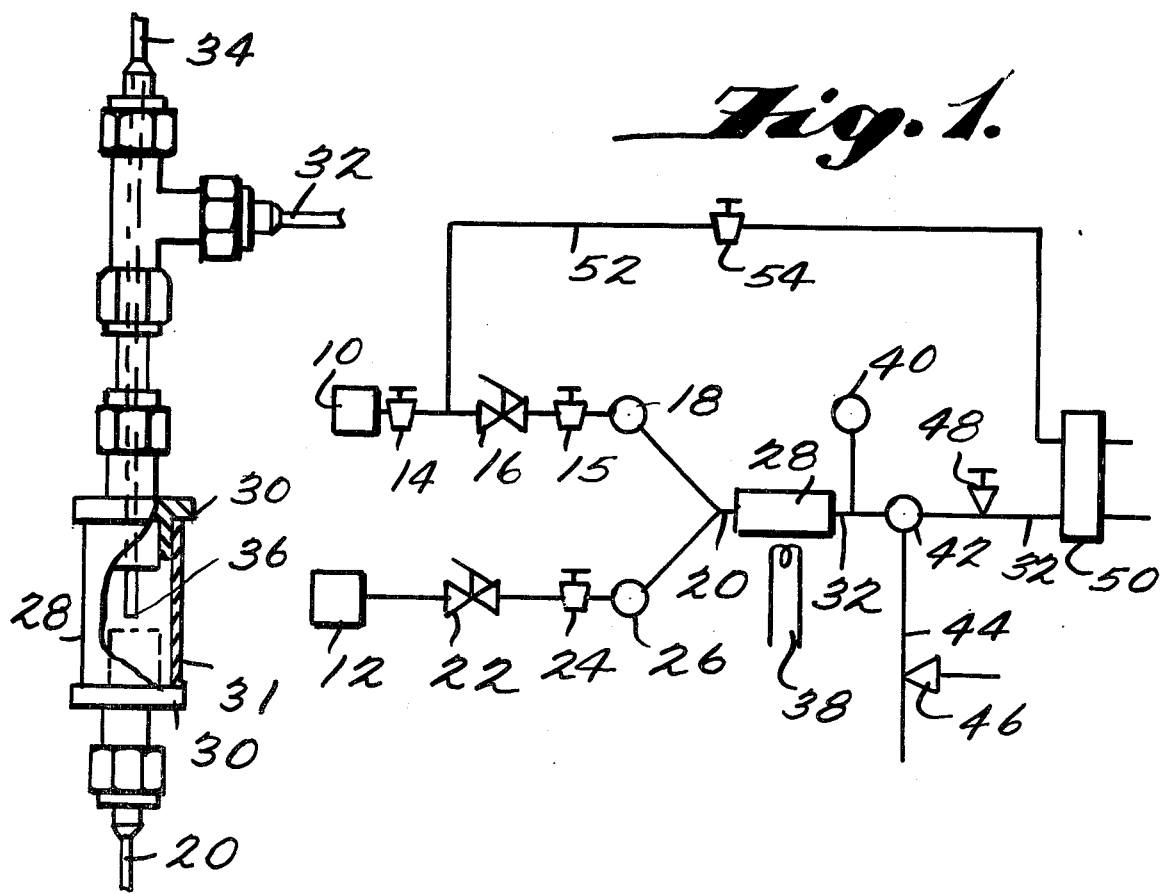

ANALYTICAL METHOD FOR DETERMINING DESORPTION ISOTHERM AND PORE SIZE DISTRIBUTION OF AN ABSORBENT MATERIAL

BACKGROUND AND BRIEF DESCRIPTION OF THE INVENTION

The present invention relates to an improved method for generating data for use in calculating a desorption isotherm and a pore size distribution characteristic of an adsorbent material such as activated carbon, alumina or silica granules or the like.

In the past, such data as is needed to derive a desorption isotherm or a pore size distribution for an adsorbent sample was obtained by loading the sample with the adsorbate gas in a static environment. Since adsorption of a gas on surface releases heat, an inconvenient delay was required before equilibrium conditions were achieved to enable measurements to be taken in such static systems.

Generally, in a system where a carrier gas continuously flows over the sample, the heat dissipation problem is circumvented but other difficulties were thought to preclude the useful application of such flow systems for obtaining data for use in the calculation of the isotherm or a pore size distribution of a sample. In particular, it was thought to be disadvantageous to measure the initial loading of the sample and poor precision was obtained as the loading on the sample decreased to zero, that is, where substantially all of the adsorbed gas is removed from the surface of the sample. Another expected difficulty with the flow method involved the removal of the final traces of the adsorbate since the partial pressure would be very low and the time interval very long, thus making precise measurements very difficult to obtain.

The method of the present invention avoids the foregoing difficulties by loading adsorbate on a sample, and then sweeping it out in a constant flow of a carrier gas while monitoring the effluent gas composition with a suitable detector such as a thermal conductivity detector or, more preferably, a gas density balance which performs a linear detection over a suitable range. The effluent composition and sample temperature are recorded as a function of time to zero loading, corresponding to complete removal of the adsorbate gas. For strongly held adsorbates, complete removal is attained by raising the temperature of the sample gradually to increase the rate of desorption. Also, the sample is intermittently agitated to keep the loading uniform.

The data accumulated by the calibrated temperature and composition detectors can be fed to a suitably programmed computer. Then a backward integration of the composition (taking into account the carrier gas flow rate) from zero to any desired loading is employed to obtain the adsorbate loading corresponding to each value of the isothermal partial pressure. However, where the sample is heated during desorption, the partial pressures are measured and corrected to the isothermal partial pressures by well known equations based on the Polanyi adsorption potential theory. The data obtained can be readily employed in standard and well known calculations to obtain the pore size distribution for the sample. Thus, a practically continuous desorption isotherm is calculated from the non-isothermal data and application of the Polanyi adsorption potential theory.

As will be apparent from the following description, the difficulty of desorbing and of measuring the low partial pressures of a strongly held adsorbate at low capacities is avoided and the time of performing the analysis to obtain the data is greatly shortened.

The foregoing and other advantages will become apparent as consideration is given to the following detailed description taken in conjunction with the accompanying drawings, in which:

BRIEF DESCRIPTION OF THE DRAWINGS

FIG. 1 is a schematic illustration of a flow diagram on an apparatus used to carry out the process;

FIG. 2 is a detailed illustration of a sample cell that can be used in the apparatus of FIG. 1; and FIG. 3 is a chart illustrating the recording of temperature and adsorbate partial pressure and the principle of the calculation used in the method of the present invention.

DETAILED DESCRIPTION OF THE INVENTION

Referring now to the drawings, there is illustrated in FIG. 1 a schematic layout of an apparatus that can be usefully employed in carrying out the method of the present invention.

Referring to FIG. 1, a gas tank 10 serves as a source of a carrier gas while tank 12 is the source of an adsorbate gas.

From tank 10, the carrier gas can be fed through conduits provided with conventional gas control devices such as a pressure controller 14, a toggle valve 16, a flow controller 15, and then preferably through a three-way switching valve 18 to an inlet tube 20. Similarly, the adsorbate gas will be passed through suitable conduits to a toggle valve 22, a flow controller 24, and then to a three-way switching valve 26 which will control flow to the inlet tube 20. It should be understood, that the three-way switching valves 18 and 26 should have an opening to vent at one of their three positions.

The sample cell or chamber 28 is shown in more detail in FIG. 2. The sample chamber 28 may be of stainless steel having sealed ends or heads 30. One of the heads 30 may be removable to permit insertion of a sample as at 31. A gas outlet is provided at 32. Both the inlet tube 20 and the outlet 32 should consist of flexible connections to permit agitation of the chamber 28. Also, a thermocouple probe 34 is provided so that its tip 36 extends into the interior of chamber 28 for the purpose of detecting the temperature thereof. Means 38 such as an electric coil are provided for heating the cell although a heated bath is preferred. As previously noted, the inlet and outlet tubes 20 and 32 should be flexible. Also, these tubes should be of sufficient length to permit some movement of the sample cell or chamber 28 for the purposes of manual agitation or the disposing of the chamber 28 on a mechanical agitator, in a bath, or adjacent to a heater 38 as may be required in carrying out the present method.

Referring again to FIG. 1, tube or conduit 32 may have a pressure gauge 40 connected thereto, although the pressure gauge may be located at other points of the flow circuit as well, as may be convenient. Downstream of the pressure gauge 40 there is preferably located another three-way switching valve 42, to which is connected a vent line 44 which may include a needle valve 46. Another needle valve 48 is preferably located downstream of the three-way valve 42.

Line 32, downstream of the needle valve 48 feeds into a gas detecting means 50 which may be of a commercially available device known as the Gow-Mac Model 24-393 which is of the semi-diffusion type. This device is used with a temperature controller and a power supply unit which has a continuously variable attenuation low-output impedance amplifier. The detector output is passed through a τ-filter network. Alternatively, a gas density balance type of detector can be used since the output of this type of detector is linear over its useful range whereas the output of a thermal conductivity detector becomes non-linear in the upper ranges.

Referring to FIG. 1 again, with a thermal cnductivity detector, a by-pass line 52 is provided and which has a flow control valve 54 to supply the carrier gas directly to the reference side of the gas detecting means.

It will be apparent to those skilled in this art that the foregoing arrangement can be varied somewhat to accommodate different types of samples or gases being employed in the process.

An example of the method of the present invention will now be given where the carrier gas is nitrogen from source tank 10 and the adsorbate gas is n-butane in tank 12. The sample 31 in chamber 28 was activated carbon, CAL lot 2131 acquired from Pittsburgh Activated Carbon Co.

The butane gas is loaded onto the sample 31 from tank 12 by being passed through the toggle valve 22, flow controller 24, three-way valve 26 and then through the sample chamber 28 and valves 42 and 46 from which the gas is allowed to vent to the atmosphere. For calibration purposes, the three-way valve 26 may be connected to a conduit which passes the adsorbate gas directly to a point where it may be mixed with a carrier gas stream from 18 and subsequently passed to the gas detector means.

In carrying out the process, the toggle valve 22 is opened after the flow control valve 24 and three-way valve 26 are properly positioned to permit flow to inlet tube 20. The adsorbate gas, which in this case is n-butane, fills the sample chamber 28 and passes out of the chamber to outlet 32 and then to vent through conduit 44 with three-way valve 42 closed to the gas detecting means 50.

The system is adjusted by the proper positioning of the valves to maintain an interior pressure of approximately 5 psig. With the sample cell filled with butane, the valves 42, 18 and 26 are closed and the chamber 28 may then be immersed in an ice bath to lower the partial pressure of the n-butane at constant loading.

The gas detecting means 50, such as the thermal conductivity detector, may be coupled directly to a computer to record its output per unit of time and partial pressures. With the unit 50 preferred, the valves 14, 15, 16 and 18 are operated to supply the carrier gas, which in this case is nitrogen, to the inlet 20 to sweep the adsorbate gas from the sample to effect desorption. The stream passing through valves 42 and 48 are controlled so that the desired pressure in the system is maintained such as at the carrier gas flow rate. After the nitrogen gas begins sweeping the chamber 28, the sample chamber 28 is removed from the ice bath and may be transferred to a heated bath or adjacent to a heating element 38 while the gas detecting means continuously monitors the composition of the gas stream from outlet 32, and the thermocouple 34 monitors the sample temperature. The sample temperature is gradually raised to increase the speed of desorption of th butane from the sample.

The thermal conductivity detector 50 continuously monitors the partial pressures of the butane and nitrogen and the process is run until the detector only senses nitrogen which, of course, corresponds to complete desorption of the butane from the sample.

Referring now to FIG. 3, there is shown a schematic chart recording of temperature and adsorbate partial pressure which is a useful illustration of the principles of the calculation method employed to obtain the desorption iostherm, which, as noted at the outset, can be used to determine the pore size distribution of a sample.

From FIG. 3, it will be noted that as the temperature T rises, the adsorbate partial pressure rises and then decreases rapidly. This is extremely useful in that the measurements can be done far more precisely and the method carried out more quickly since desorption will occur in much less time than with the static method, previously employed.

Where a linear gas detecting means is employed, backward integration can be employed without the use of a computer (e.g., by use of a disc integrator) to determine the loading of the sample at any given partial pressure.

In determining the entire isotherm, an adsorption isotherm point, the loading and the partial pressure at some fixed temperature, is determined at time Q as follows: (1) the amount of adsorbate is proportional to the area OPQ under the partial pressure curve (the proportionality constant is readily calculated from the flow rate and the gas law); (2) the partial pressure P', at temperature T', is calculated from P and T (the measured values) by the equation:

$$T \log (P_s/P) = T' \log(P'_{40\,s}/P')$$

where $P'_s$ and $P_2$ are the saturation pressures of the vapor at T' and T.

For a comparison of the results of the method to actual experimental measurements, reference should be had to the article appearing in Analytical Chemistry, Volume 29, No. 7 of June, 1977, pages 991-994.

While the foregoing has been a description of the preferred embodiment of the present invention, it will be obvious to those skilled in this art that various modifications may be made therein without departing from the spirit and scope of the present invention as defined in the appended claims.

What is claimed is:

1. A method of generating data for use in calculating a desorption isotherm for an adsorbent material comprising the steps of:
    passing an adsorbate gas through a cell containing a sample of the adsorbent material until the surface of the sample is loaded to the desired extent with the adsorbate gas,
    shutting off the flow of the adsorbate gas,
    gradually raising the temperature of the sample while flowing a carrier gas through the cell to remove the adsorbate gas from the surface of the sample and agitating the sample at periodic intervals while continuously detecting and recording the sample temperature and the composition of the carrier and adsorbate gas mixture flowing out of the cell per unit of time until at least only the carrier gas is detected.

2. The method as claimed in claim 1 including the step of, after shutting off the flow of the adsorbate gas to the cell, reducing the partial pressure of the adsorbate gas in the cell by cooling the cell to effect saturation of the surface of the sample with the adsorbate gas.

3. The method as claimed in claim 1 wherein said adsorbate gas is n-butane and said carrier gas is nitrogen.

4. The method as claimed in claim 3 wherein said sample is activated carbon and the temperature of said sample is raised from approximately 0° C. to approximately 350° C.

5. The method as claimed in claim 3 wherein said method is carried out with the gases maintained at a pressure of approximately 5 psig in said cell.

* * * * *

UNITED STATES PATENT AND TRADEMARK OFFICE
CERTIFICATE OF CORRECTION

PATENT NO. : 4,149,402
DATED : April 17, 1979
INVENTOR(S) : Milton Manes

It is certified that error appears in the above-identified patent and that said Letters Patent are hereby corrected as shown below:

Column 3, line 13, change "cnductivity" to --conductivity--.

Column 3, line 68, change "th" to --the--.

Column 4, line 34, correct the equation to read:

--$T \log(P_s/P) = T' \log(P'_s/P')$--.

Column 4, line 36, change "$P_2$" to --$P_s$--.

Signed and Sealed this

Eighteenth Day of September 1979

[SEAL]

Attest:

LUTRELLE F. PARKER

*Attesting Officer*   *Acting Commissioner of Patents and Trademarks*